US012029632B2

(12) United States Patent
Dushyantha et al.

(10) Patent No.: US 12,029,632 B2
(45) Date of Patent: Jul. 9, 2024

(54) PERMEABLE UNDERGARMENT, A DETACHABLE POUCH AND AN UNDERGARMENT SYSTEM THEREOF

(71) Applicant: MAS Innovation (Private) Limited, Colombo (LK)

(72) Inventors: Mapitiyage Don Janith Dushyantha, Colombo (LK); Ranil Vitarana, Colombo (LK)

(73) Assignee: MAS Innovation (Private) Limited, Colombo (LK)

( * ) Notice: Subject to any disclaimer, the term of this patent is extended or adjusted under 35 U.S.C. 154(b) by 965 days.

(21) Appl. No.: 16/628,129

(22) PCT Filed: Jul. 3, 2018

(86) PCT No.: PCT/SG2018/050324
§ 371 (c)(1),
(2) Date: Jan. 2, 2020

(87) PCT Pub. No.: WO2019/009805
PCT Pub. Date: Jan. 10, 2019

(65) Prior Publication Data
US 2020/0222250 A1     Jul. 16, 2020

(30) Foreign Application Priority Data
Jul. 3, 2017 (SG) ............................ 10201705451V

(51) Int. Cl.
*A61F 13/49* (2006.01)
*A61F 13/496* (2006.01)
(Continued)

(52) U.S. Cl.
CPC .. *A61F 13/49006* (2013.01); *A61F 13/49004* (2013.01); *A61F 13/496* (2013.01); *A61F 13/74* (2013.01); *A61F 13/84* (2013.01)

(58) Field of Classification Search
CPC ...... A61F 13/49003; A61F 2013/49063; A61F 13/74; A61F 13/66; A61F 13/495; A61F 5/451; A61F 5/453; A61F 5/455
See application file for complete search history.

(56) References Cited

U.S. PATENT DOCUMENTS 4,886,508 A * 12/1989 Washington ............ A61F 5/455
604/347
6,623,466 B1 9/2003 Richardson
(Continued)

FOREIGN PATENT DOCUMENTS

| WO | WO-01/24751 | 4/2001 |
| WO | WO-2014/176677 | 11/2014 |
| WO | WO-2015/039218 | 3/2015 |

OTHER PUBLICATIONS

International Search Report and Written Opinion for International Patent Application No. PCT/SG2018/050324, dated Sep. 26, 2018 (13 pages).

*Primary Examiner* — Sarah Al Hashimi
*Assistant Examiner* — Meagan Ngo
(74) *Attorney, Agent, or Firm* — Mintz, Levin, Cohn, Ferris, Glovsky and Popeo, P.C.

(57) ABSTRACT

A permeable undergarment comprising, a top portion and a bottom portion wherein the top portion of the undergarment is provided by a waistband, and the bottom portion of the undergarment is provided with the permeable layer. The permeable layer comprises a mesh of wicking fibres to wick the body fluids discharged from a user and transfers the body fluids through the permeable layer. A detachable pouch having a base layer and a plurality of side walls is also provided. The detachable pouch is defined such that, the base layer and the plurality of side walls together form a housing region. The housing region may house at least one absorption pad. The detachable pouch may be detachably (Continued)

attached or joined to the undergarment such that, the body fluids discharged from the user flows through the permeable layer and into the detachable pouch for absorption by the at least one absorption pad.

8 Claims, 5 Drawing Sheets

(51) Int. Cl.
*A61F 13/74* (2006.01)
*A61F 13/84* (2006.01)

(56) References Cited

U.S. PATENT DOCUMENTS

| 2003/0028161 A1* | 2/2003 | Carballo | A61F 5/453 |
| | | | 604/351 |
| 2014/0018756 A1* | 1/2014 | De Bruin | A61F 13/505 |
| | | | 604/385.01 |
| 2015/0157513 A1* | 6/2015 | Hovey | A61F 13/505 |
| | | | 604/385.15 |

* cited by examiner

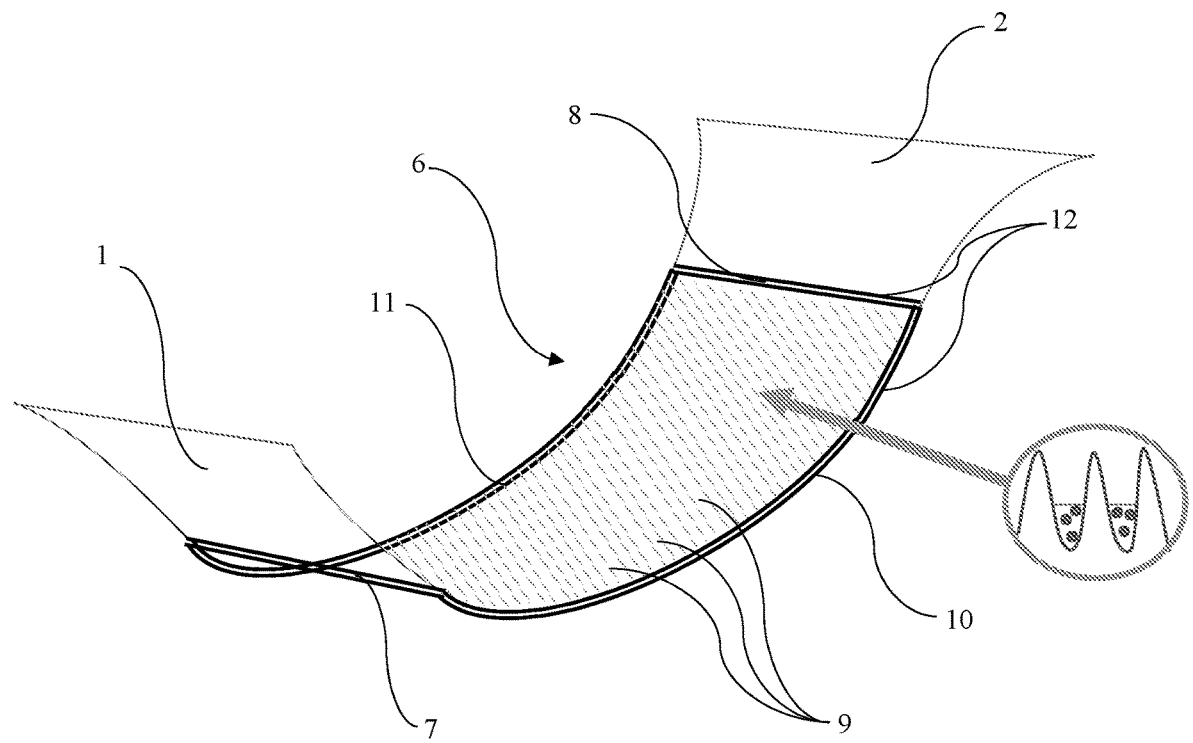
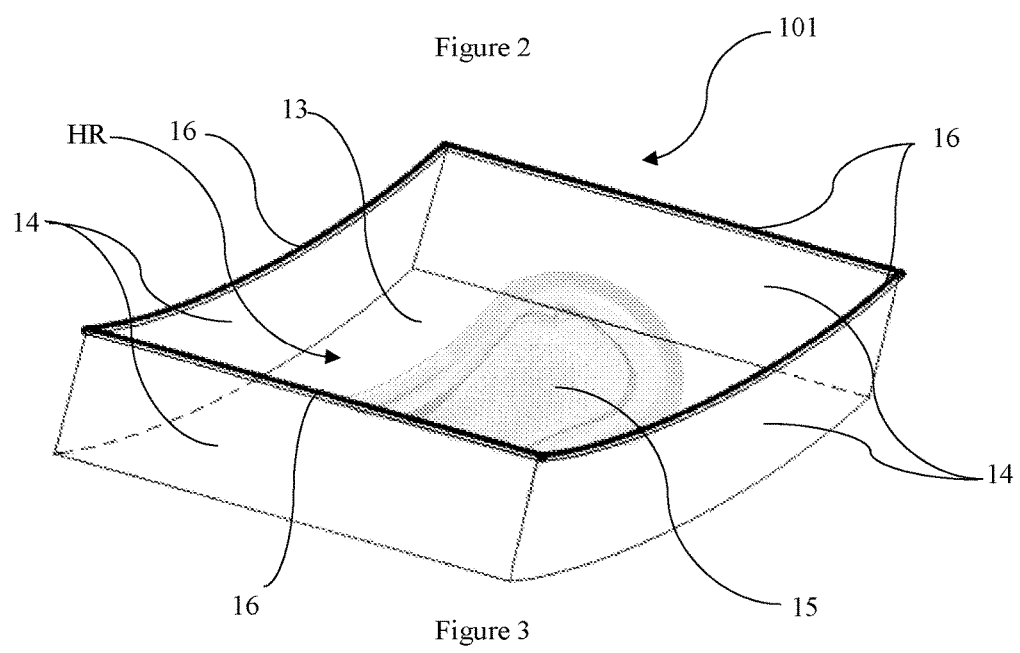
Figure 2
Figure 3

PERMEABLE UNDERGARMENT, A DETACHABLE POUCH AND AN UNDERGARMENT SYSTEM THEREOF

CROSS-REFERENCES TO RELATED APPLICATIONS

This application is a U.S. National Phase Application of PCT International Application No. PCT/SG2018/050324, filed on Jul. 3, 2018, which is an International Application of and claims the benefit of priority to Singapore Patent Application No. 10201705451V, filed on Jul. 3, 2017.

TECHNICAL FIELD

The present disclosure relates to the field of undergarments or underclothing. More particularly, the present disclosure relates to a permeable undergarment for absorbing body fluids discharged from a user.

BACKGROUND OF THE DISCLOSURE

Conventionally, the marketplace for absorbents of body fluids from users is currently dominated by disposable products such as liners, pads, diapers and tampons. While such disposable products made of nonwoven materials have high functionality in terms of high wicking, high absorbency and leak-proof ability. However, they tend to be bulky, visible if worn under certain clothing and make the user feel like they have a "special condition".

Such disposable products are largely available in the market today. There are several products that have absorption properties which come knitted or fixed to a wearable undergarment such as a panty. However, these undergarments are not reusable and need to be disposed after use. A new undergarment/diaper needs to be purchased each and every time after usage. In some scenarios, the body fluids from the user may even soil the undergarment and may prevent re-usage or could cause an awkward situation for the user.

The current marketplace also has fully reusable/fabric/textile solutions to help manage the absorption of body fluids. Examples include, period or menstrual cycle underwear and urinary incontinence underwear. However, due to technical limitations, the amount of body fluid that a fabric can absorb is limited.

The information disclosed in this background of the disclosure section is only for enhancement of understanding of the general background of the disclosure and should not be taken as an acknowledgement or any form of suggestion that this information forms prior art already known to a person skilled in the art.

SUMMARY OF THE DISCLOSURE

One or more shortcomings of the prior art may be overcome, and additional advantages may be provided through the present disclosure. Additional features and advantages may be realized through the techniques of the present disclosure. Other embodiments and aspects of the disclosure are described in detail herein and are considered a part of the claimed disclosure.

Disclosed herein is a permeable undergarment comprising a first section forming a front side of the undergarment, extending from a top portion to a bottom portion. A second section is provided opposite to the first section and forms a rear side of the undergarment, extending from the top portion to the bottom portion. The first section and the second section are joined to a waistband at the top portion of the undergarment. A first leg opening and a second leg opening is defined in-between the first section and the second section. The openings are on adjacent sides of a crotch region. A permeable layer provided at the crotch region, wherein the permeable layer connects the first section and the second section of the undergarment at the bottom portion, and allows flow of body fluids from a user through the permeable layer.

In an embodiment, the first section of the undergarment at the bottom portion is connected to a first joining edge of the permeable layer.

In an embodiment, the second section of the undergarment at the bottom portion is connected to a second joining edge of the permeable layer.

In an embodiment, the permeable layer comprises a mesh of wicking fibres to wick the body fluids off the user and transfers the body fluids through the permeable layer.

In an embodiment, the mesh of wicking fibres, at its tip portions are coated with fluid repellent solution to prevent stagnation of the body fluids discharged from the user on the mesh of wicking fibres.

In an embodiment, the first joining edge, the second joining edge, a first side edge and a second side edge of the permeable layer are equipped with gripping layers, to grip the permeable layer on skin of the user.

In an embodiment, the gripping layers are adhesively joined to the first joining edge, the second joining edge, the first side edge and the second side edge.

In an embodiment, the permeable layer is detachable from the first section and the second section of the undergarment.

Disclosed herein a detachable pouch for a permeable undergarment comprising a base layer. A plurality of side walls extending from the base layer, wherein each side edge of the plurality of side walls are connected to one another, thereby defining the detachable pouch. A housing region defined on the base layer, at an inner portion of the plurality of side walls, wherein the housing region is configured to house at least one absorption pad. A plurality of fasteners equipped on each of a top edge of the plurality of side walls, fastens the detachable pouch onto an outer surface of the undergarment to collect and absorb body fluids discharged from a user.

In an embodiment, the detachable pouch is attached to the outer surface at the crotch region of the undergarment.

In an embodiment, each of the top edges of the plurality of side walls is attached to each edge of a permeable layer on the outer surface of the undergarment for collecting the body fluids discharged from the user.

In an embodiment, the body fluids discharged from the user are received in the detachable pouch through the permeable layer and absorbed by the at least one absorption pad.

In an embodiment, the base layer is configured as the at least one absorption pad to absorb the body fluids discharged from the user.

In an embodiment, the at least one absorption pad may be placed within the housing region through an opening defined at the top portion of the detachable pouch.

In an embodiment, the at least one absorption pad is placed within the housing region through the opening defined at any of a side portion of the detachable pouch.

In an embodiment, a top flap and a bottom flap is provided at one of the side portion which is operable between an open condition and a closed condition, for inserting and removing the at least one absorption pad.

In an embodiment, the plurality of side walls extend upwardly from the base layer up to a predetermined length to prevent leakage of the body fluids discharged by the user from the housing region.

In an embodiment, the plurality of fasteners are adhesively joined on the top edges of the plurality of side walls to securely attach the detachable pouch for collecting the body fluids discharged from the user.

In an embodiment, the detachable pouch is treated with an anti-fouling solution, an anti-microbial solution, an odour treatment solution and the like.

Disclosed is an undergarment system with a permeable layer and a detachable pouch. A first section forms a front side of the undergarment, extending from a top portion to a bottom portion. A second section provided opposite to the first section and forming a rear side of the undergarment, extending from the top portion to the bottom portion, wherein the first section and the second section are joined to a waistband at the top portion of the undergarment. A first leg opening and a second leg opening defined in-between the first section and the second section, and on adjacent sides of a crotch region. The permeable layer provided at the crotch region, wherein the permeable layer connects the first section and the second section of the undergarment at the bottom portion, and allows flow of body fluids from the user through the permeable layer. The detachable pouch comprises a base layer and a plurality of side walls extending from the base layer, wherein each side edge of the plurality of side walls are connected to one another, thereby defining the detachable pouch. A housing region defined on the base layer, at an inner portion of the plurality of side walls, wherein the housing region is configured to house at least one absorption pad. A plurality of fasteners equipped on each of a top edge of the plurality of side walls, fastens the detachable pouch onto an outer surface of the undergarment to collect and absorb body fluids discharged from a user.

BRIEF DESCRIPTION OF THE ACCOMPANYING DRAWINGS

The accompanying drawings, which are incorporated in and constitute a part of this disclosure, illustrate exemplary embodiments and, together with the description, serve to explain the disclosed principles. In the figures, reference numbers are used to identify parts/aspects and the figures in which they first appear. The same numbers are used throughout the figures to reference like features and components. Some embodiments of system and/or product in accordance with embodiments of the present subject matter are now described, by way of example only, and with reference to the accompanying figures, in which:

FIG. 2 shows a perspective view of the permeable undergarment with a permeable layer in accordance with some embodiments of the present disclosure.

FIG. 3 shows a perspective view of a detachable pouch for the permeable undergarment in accordance with some embodiments of the present disclosure.

Figure 1:
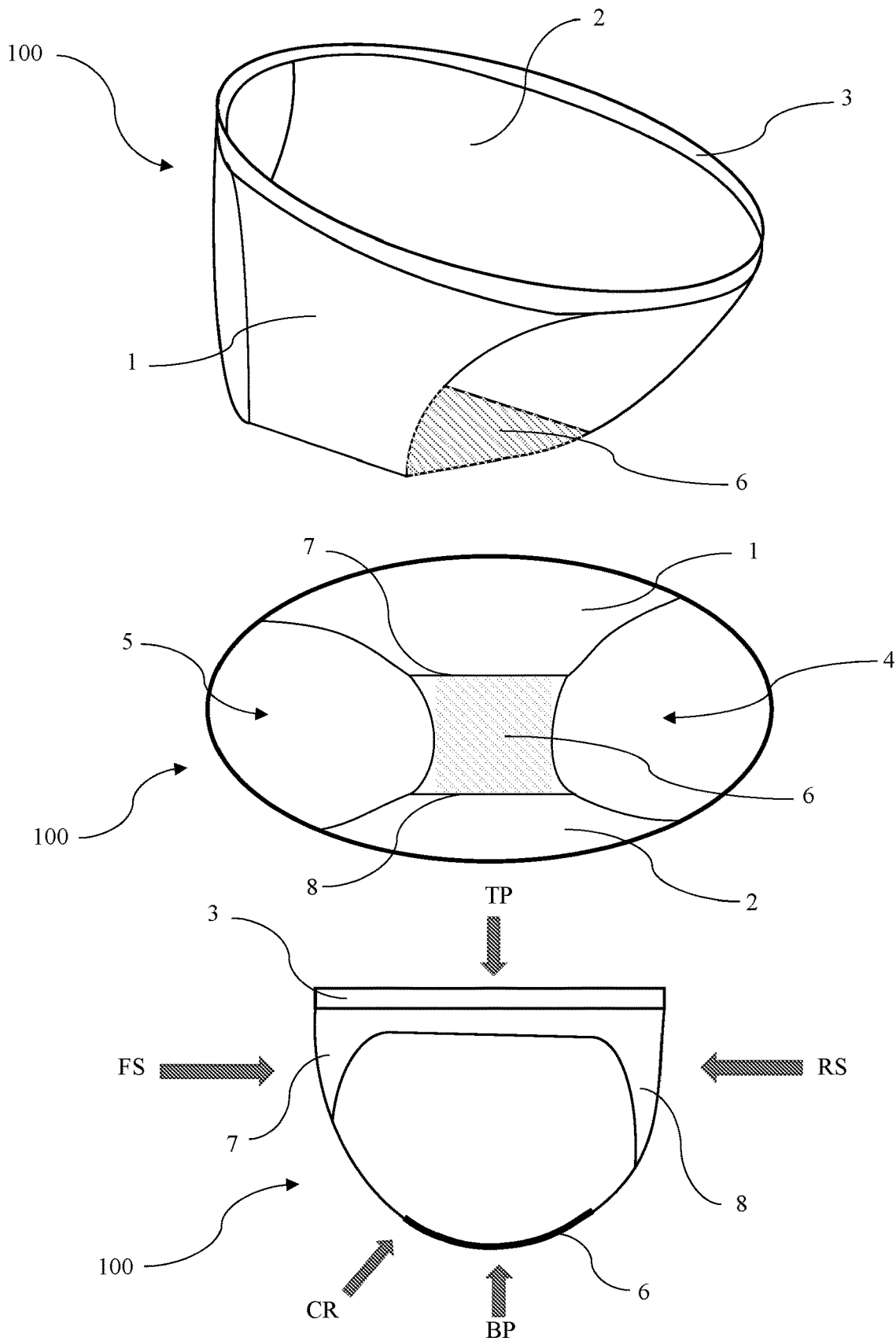
FIG. 1 shows perspective, top and side views of an exemplary permeable undergarment in accordance with some embodiments of the present disclosure.

It should be appreciated by those skilled in the art that any diagrams herein represent conceptual views of illustrative product and system embodying the principles of the present subject matter.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the forms disclosed, but on the contrary, the disclosure is to cover all modifications, equivalents, and alternative falling within the scope of the disclosure.

The terms "comprises", "comprising", "includes" or any other variations thereof, are intended to cover a non-exclusive inclusion, such that a setup, device or method that includes a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

Disclosed herein is a permeable undergarment having a permeable layer. The undergarment is constructed such that a first section and a second section of the undergarment forms a front side and rear side of the undergarment respectively. The undergarment further comprises, a top portion and a bottom portion wherein the top portion of the undergarment is provided by a waistband, and the bottom portion of the undergarment is provided with the permeable layer. The permeable layer comprises a mesh of wicking fibres to wick the body fluids discharged from a user and transfers the body fluids through the permeable layer. A detachable pouch having a base layer and a plurality of side walls is also provided. The detachable pouch is defined such that, the base layer and the plurality of side walls together form a housing region. The housing region may house at least one absorption pad. The detachable pouch is then fixed to the undergarment. The detachable pouch may be detachably attached or joined to the undergarment such that, the body fluids discharged from the user flows through the permeable layer and into the detachable pouch for absorption by the at least one absorption pad.

Therefore, using such an undergarment which has the permeable layer aids in easy passage or flow of the body fluids discharged from the user. Additionally, the detachable pouch which is fixed to the undergarment absorbs these body fluids. The user can dispose the detachable pouch and reuse the undergarment based on requirement Moreover, the permeable layer provided in the undergarment can also be configured to be detached and disposed off or configured to be fixed to the undergarment and capable of being reused.

In the following detailed description of the embodiments of the disclosure, reference is made to the accompanying drawings that form a part hereof, and in which are shown by way of illustrating specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1 shows a perspective, a top and side views of an exemplary permeable undergarment (100) [herein referred to as "undergarment (100)"]. The undergarment (100) as illustrated in the perspective view depicts a first section (1) that forms a front side (FS) of the undergarment (100). The first section (1) extends from a top portion (TP) up to a bottom portion (BP) for a predetermined length. Similarly, a second section (2) that is provided opposite to the first section (1) extends from the top portion (TP) to the bottom portion (BP), thereby forming a rear side (RS) of the undergarment (100). The first section (1) and the second section (2) are designed such that, at the top portion (TP) of the undergarment (100), both the first section (1) and the second section (2) are joined to a waistband (3). In an embodiment, the waistband (3) may be a strip of clothing that effectively covers around a waistline of a user in order to grip the undergarment (100) onto the body of the user. In a preferred embodiment, the waistband (3) may include, but not limited to, at least one of an elastic member, an elastic garment strip, a lace type garment strip, a string type garment strip or any other garment strip that serves the purpose of securing the undergarment (100) on the body of the user.

Further, the first section (1) and the second section (2) of the undergarment (100) at the bottom portion (BP) is connected together by a permeable layer (6). The permeable layer (6) is located at a crotch region (CR) of the undergarment (100), wherein the permeable layer (6) connects the first section (1) and the second section (2). This connection of the first section (1) and the second section (2) defines a first leg opening (4) and a second leg opening (5) on adjacent sides of the crotch region (CR). In an embodiment, the first leg opening (4) and the second leg opening (5), defined in-between the first section (1) and the second section (2) is configured to snuggly fit onto the leg portion, preferably thigh portion of the user. In a preferred embodiment, the first leg opening (4) and the second leg opening (5) may be provided with elasticized leg bands such that, the undergarment (100) is securely fit onto the body of the user. In some embodiments, the size of the leg openings may vary depending upon the dimensional sizes of the first section (1) and the second section (2). Additionally, the dimensional sizes of the crotch region (CR) may also affect the size of the leg openings. However, the dimensional fit and securement of the undergarment (100) may depend upon the type of undergarment (100) and the size of the undergarment (100) to accommodate users ranging from infants to adults.

FIG. 2 shows a perspective view of the undergarment (100) with the permeable layer (6). The permeable layer (6) is located at the crotch region (CR) of the undergarment (100) connecting the first section (1) and the second section (2) as disclosed in the above paragraphs. The permeable layer (6) comprises of a first joining edge (7) and a second joining edge (8) located opposite to each other and separated by a mesh of wicking fibres (9) [herein referred to as wicking fibres]. Additionally, the permeable layer (6) further comprises of, a first side edge (10) and a second side edge (11) located opposite to each other and connected to the first joining edge (7) and the second joining edge (8), thereby forming the boundary of the permeable layer (6). In an embodiment, the first joining edge (7) is connected to the first section (1) of the undergarment (100). Similarly, the second joining edge (8) is connected to the second section (2) of the undergarment (100). In a preferred embodiment, the first joining edge (7) and the second joining edge (8) of the permeable layer (6) may be detachably attached or joined to the first section (1) and the second section (2) of the undergarment (100). The first joining edge (7) and the second joining edge (8), along their entire lengths, may be equipped with attaching or joining means such as but not limiting to Velcro strips, detachable adhesive tapes, silicone sticky tapes, plurality of snap-fitting buttons or any other attaching or joining means that serves the purpose of attaching or joining the permeable layer (6) detachably, to the undergarment (100). In some embodiments, the first joining edge (7) and the second joining edge (8) of the permeable layer (6) may be permanently attached or permanently joined to the first section (1) and the second section (2) of the undergarment (100) respectively. The first joining edge (7) and the second joining edge (8) may be attached or joined to the undergarment (100) by at least one of adhesive bonding, stitching, knitting or any other process that serves the purpose of attaching or joining the permeable layer (6) permanently, to the undergarment (100).

In some embodiments, the first joining edge (7), the second joining edge (8), the first side edge (10) and the second side edge (11) is equipped with gripping layers (12). The gripping layers (12) are provided on inner edges of the undergarment (100) that is in contact with skin of the user. These gripping layers (12) allows the edges of the permeable layer (6) to be in contact with the skin of the user so that, the permeable layer (6) is always present at the catchment area to wick or absorb the body fluids discharged from the user. In an embodiment, the gripping layers (12) are at least one of grip tapes, slick wraps, anti-slip wraps, silicone coated tapes, adhesive bonding tapes or any other layers/wraps that serves the purpose of gripping the edges of the permeable layer (6) to the skin of the user.

Further, the permeable layer (6) comprises the wicking fibres (9) that are provided within the entire boundary of the permeable layer (6). The wicking fibres (9) extend from one boundary edge of the permeable layer (6) to the other boundary edge. The wicking fibres (9) are so provided to wick or absorb any of the body fluids discharged by the user. In an embodiment, the pattern or design of the wicking fibres (9) is constructed such that, the body fluids can easily flow out of the permeable layer (6). In a preferred embodiment, tip portions of the wicking fibres (9) are coated with fluid repellent solution. The fluid repellent solution coated on to the tip portions, prevents stagnation of the body fluids discharged from the user. Additionally, the fluid repellent solution also provides breathability to the skin, at the catchment region. This not only prevents discomfort and feeling of wettability, but also prevents any type of skin irritation or formation of skin rash at sensitive parts of the skin of the user. In an embodiment, the fluid repellent solution is at least one of but not limited to silicone coating, hydrophilic softeners, plasma coating or any other fluid repellent solution or surface modification treatment coatings that serves the purpose.

Further, the permeable layer (6) comprising the wicking fibres (9) that can be reusable by simply cleaning or washing of the soiled areas. In some embodiments, the permeable layer (6) can be completely detachable and the permeable layer (6) can also be reusable or disposed. Additionally, a fresh and clean permeable layer (6) can also be attached to the undergarment (100) for usage. In an embodiment, the wicking fibres (9) may be replaced with plurality of voids or holes [not shown in figures] that allow passage of body fluids discharged from the user. The plurality of voids or holes may be so provided in the permeable layer (6) such that, the entire catchment area can be covered for effective absorption of the body fluids from the user. In some embodiments, the permeable layer (6), including the edges of the permeable layer (6) and the wicking fibres (9) may be treated with an anti-fouling solution, an anti-microbial solution, an odour treatment solution and the like.

Further, the crotch region (CR) of the undergarment (100), at the region where the permeable layer (6) is attached may be provided with provisions for attaching or joining a detachable pouch (101). In an embodiment, the body fluids discharged from the user flows through the permeable layer (6) and collects in the detachable pouch (101). The first joining edge (7), the second joining edge (8), the first side edge (10) and the second side edge (11) on its outer surface, i.e. the outer surface of the undergarment (100), may be provided with provisions such as, but not limited to, Velcro strips, detachable adhesive tapes, silicone sticky tapes, plurality of snap-fitting buttons or any other attaching or joining means that serves the purpose of attaching or joining the detachable pouch to the undergarment (100). In an embodiment, the detachable pouch (101) of the present disclosure is reusable and washable.

FIG. 3 shows a perspective view of the detachable pouch (101) for the undergarment (100). The detachable pouch (101) is defined by a base layer (13), wherein a plurality of side walls (14) extend upwardly from the base layer (13). The plurality of side walls (14) so extended are each connected at their edges to form a wall around the base layer (13). This configuration of the base layer (13) and the plurality of side walls (14) therein forms a housing region (HR). The housing region (HR) which is defined on the base layer (13), at an inner portion of the plurality of side walls (14) is configured to accommodate at least one absorption pad (15). In an embodiment, the housing region (HR) of the detachable pouch (101) is accessible from the top defined by an opening (17) for placement and removal of the at least one absorption pad (15). In a preferred embodiment, each of a top edge of the plurality of side walls (14) are provided with a plurality of fasteners (16). The plurality of fasteners (16) is configured to attach onto the provisions provided on the outer surface of the undergarment (100), preferably at the region where the permeable layer (6) is located. The user, in operation may simply attach the detachable pouch (101) onto the undergarment (100) in order to collect the body fluids within the detachable pouch (101). In some embodiments, the plurality of fasteners (16) is at least one of, but not limited to, Velcro strips, detachable adhesive tapes, silicone sticky tapes, plurality of snap-fitting buttons or any other fastening means that serves the purpose of fastening the detachable pouch to the undergarment (100). In an embodiment, the at least one absorption pad (15) housed in the detachable pouch (101) may be any of a disposable or reusable pad available in the market. In a preferred embodiment, the at least one absorption pad (15) housed in the detachable pouch (101) is disposable. In one embodiment, the at least one absorption pad (15) is capable of absorbing body fluids including but not limiting menstrual fluid and urine.

Further, in some embodiments, the base layer (13) of the detachable pouch (101) may be configured to be the at least one absorption pad (15). The base layer (13) may be designed such that the at least one absorption pad (15) may be integrated with the detachable pouch (101) to absorb the body fluids discharged from the user, without having to place the at least one absorption pad (15) separately. In an embodiment, the base layer (13) may be manufactured of a material that can absorb body fluids such as but not limiting to a fabric material, a reusable non-woven fabric material, or any other material that may be used for absorbing fluids.

Figure 6:
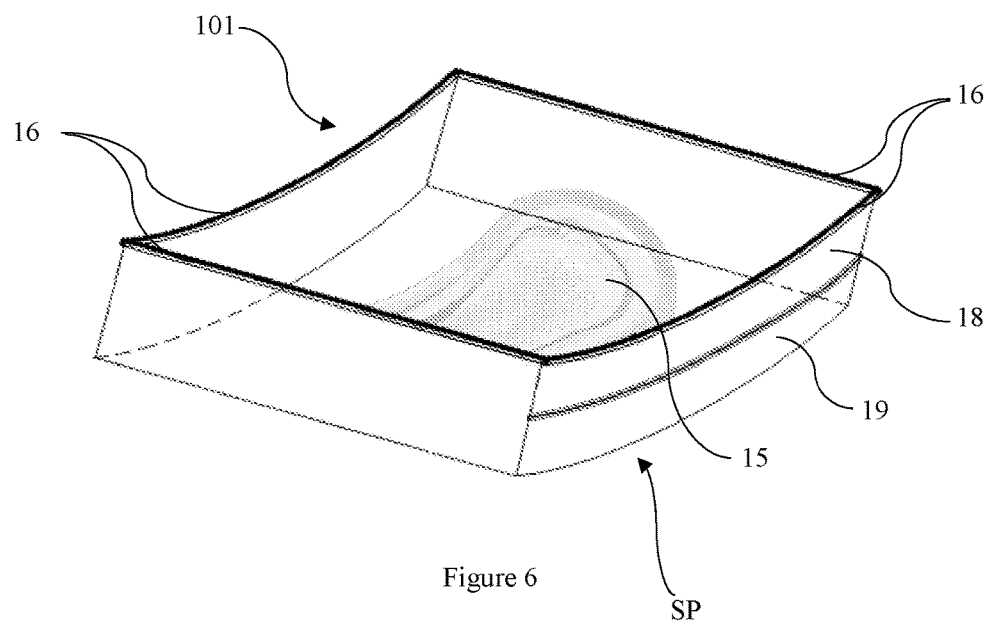
FIG. 6 shows perspective view of the detachable pouch with an opening in closed condition, provided on a side portion, in accordance with some embodiments of the present disclosure.
Figure 7:
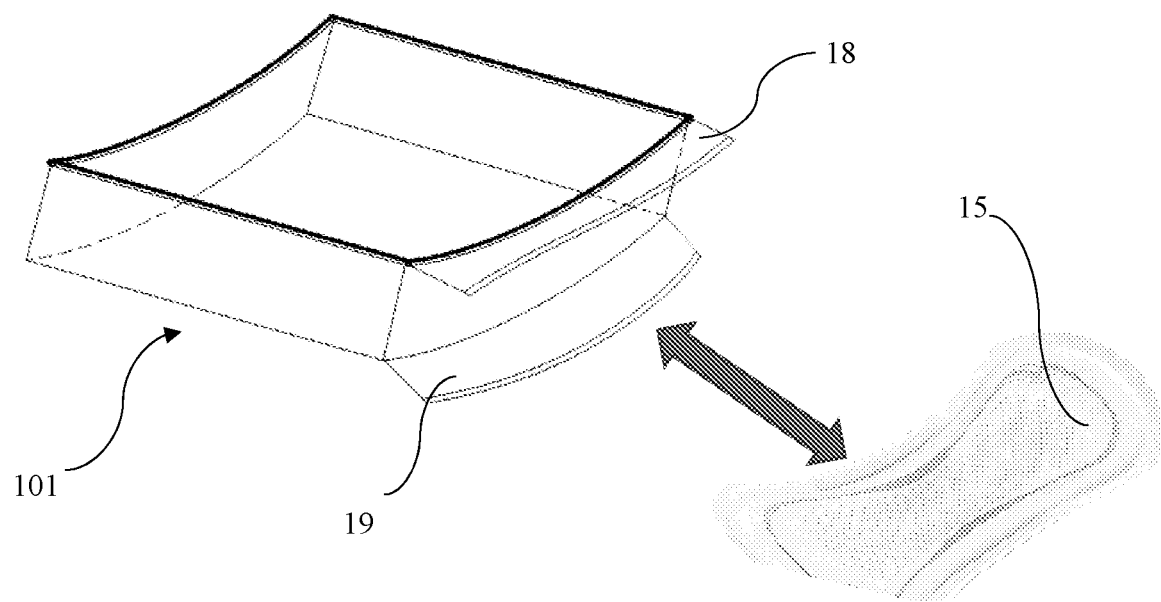
FIG. 7 shows perspective view of the detachable pouch with the opening in open condition, in accordance with some embodiments of the present disclosure.

In an embodiment, the plurality of side walls (14) of the detachable pouch (101) are configured such that, the body fluids collected within the housing region (HR) stays within the housing region (HR) and prevents leakage of the body fluids from the housing region (HR). Since the plurality of walls (14) are in a raised configuration from the base layer (13), the body fluids stays within the housing region (HR). In an embodiment, the plurality of side walls (14) may be manufactured from at least one of, but not limiting to textile material, knitted fabric material, woven fabrics, reusable fabric material, non-woven fabrics which may have an affinity for absorbing fluid and also prevent leaks. In some embodiments, the plurality of side walls (14) and the detachable pouch (101) may also be treated with leak proof coatings with an added advantage of washing and reusing. Further, referring to FIGS. 6 and 7, the detachable pouch (101) has an opening (17) defined at any of the side portion (SP) of the detachable pouch (101). The opening (17) comprises a top flap (18) and a bottom flap (19) which is operable between an open condition (OC) and a closed condition (CC) for inserting and/or removing the at least one absorption pad (15). The top flap (18) and the bottom flap (19) are attached to top and bottom edges of the plurality of side walls (14) which is an extension of the detachable pouch (101). In an embodiment, the top flap (18) at its outwardly opening tip is equipped with attaching or joining means [not shown in figures], such as but not limited to Velcro strips, detachable adhesive tapes, silicone sticky tapes, plurality of snap-fitting buttons or any other attaching or joining means that serves the purpose of joining the top flap (18) with the bottom flap (19). However, the above mentioned aspects of providing attaching or joining means is not limited to only the top flap (18), but can also be provided even on the bottom flap (19) or vice-versa. Hence, this should not be construed as a limiting feature, and should be considered as only an illustrative embodiment.

Further, in some embodiments, the detachable pouch (101), including the base layer (13) and the plurality of side walls (14) may be treated with an anti-fouling solution, an anti-microbial solution, an odour treatment solution and the like.

Figure 4:
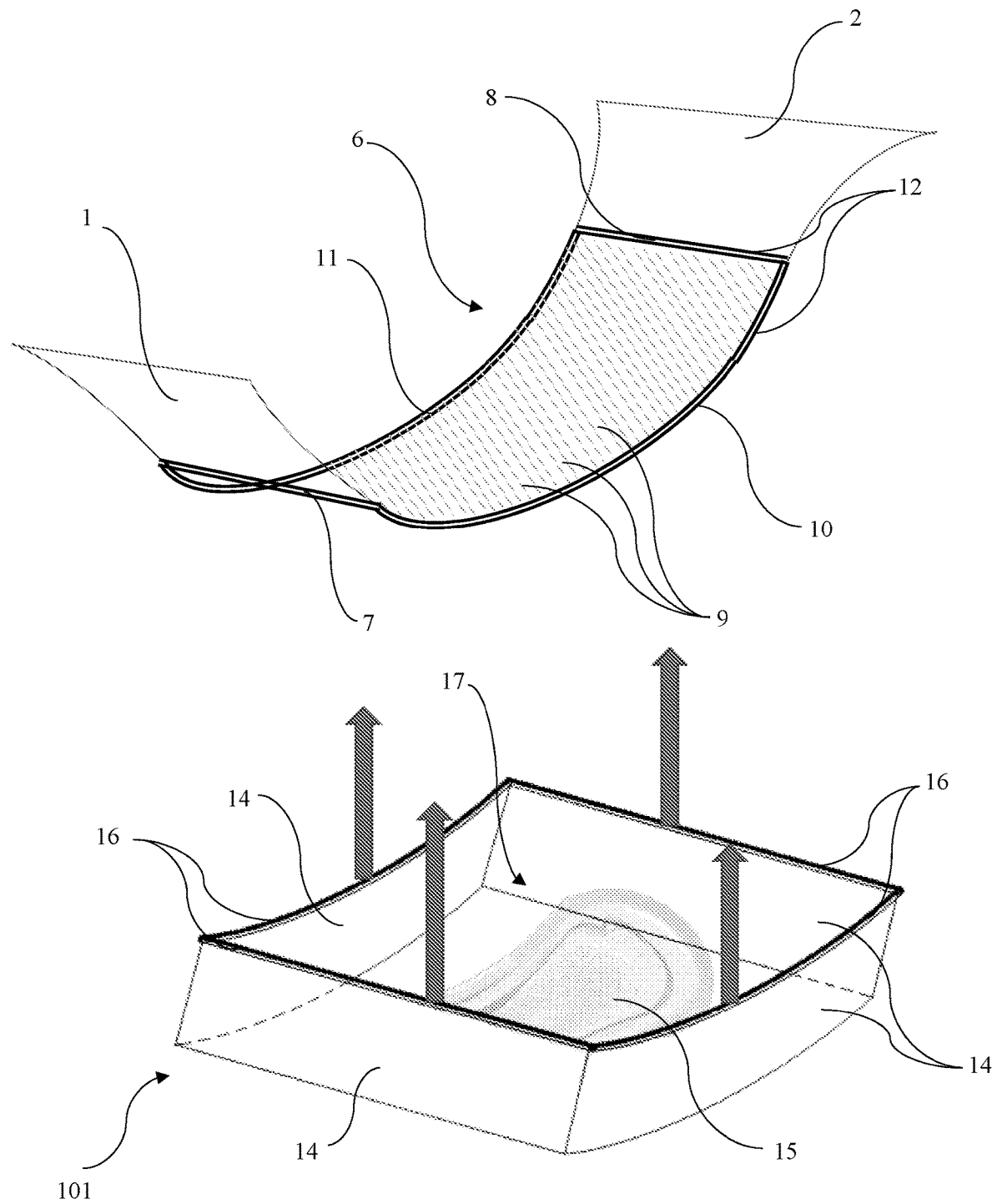
FIG. 4 shows an exploded view of the detachable pouch being fixed to an outer surface of the permeable undergarment at the permeable layer in accordance with some embodiments of the present disclosure.

FIG. 4 illustrates an exploded view of the detachable pouch (101). The detachable pouch (101) in operation can be fixed and detached from the outer surface of the undergarment (100) preferably at the permeable layer (6). The user may place the at least one absorption pad (15) within the housing region (HR) of the detachable pouch (101) prior to attaching to the undergarment (100). In cases where the base layer (13) is configured as the at least one absorption pad (15), the user may not need to place a separate absorption pad (15). The base layer (13) in such a configuration may be capable of absorbing light amount of body fluids without having to use the at least one absorption pad (15). However, the user may opt to have more than one absorption pad (15) to be placed within the housing region (HR) of the detachable pouch (101). Once the at least one absorption pad (15) is placed in the housing region (HR) the user can simply align the plurality of the fasteners (16) to the provisions provided on the outer surface of the undergarment (100), at the region where the permeable layer (6) is located. Once the detachable pouch (101) is fixed to the undergarment (100), it forms an undergarment system (A) wherein the body fluids discharged from the user are absorbed by the wicking fibres (9) and flows through the permeable layer (6) into the detachable pouch (101). The detachable pouch (101) equipped with the at least one absorption pad (15), absorbs the body fluids.

Figure 5:
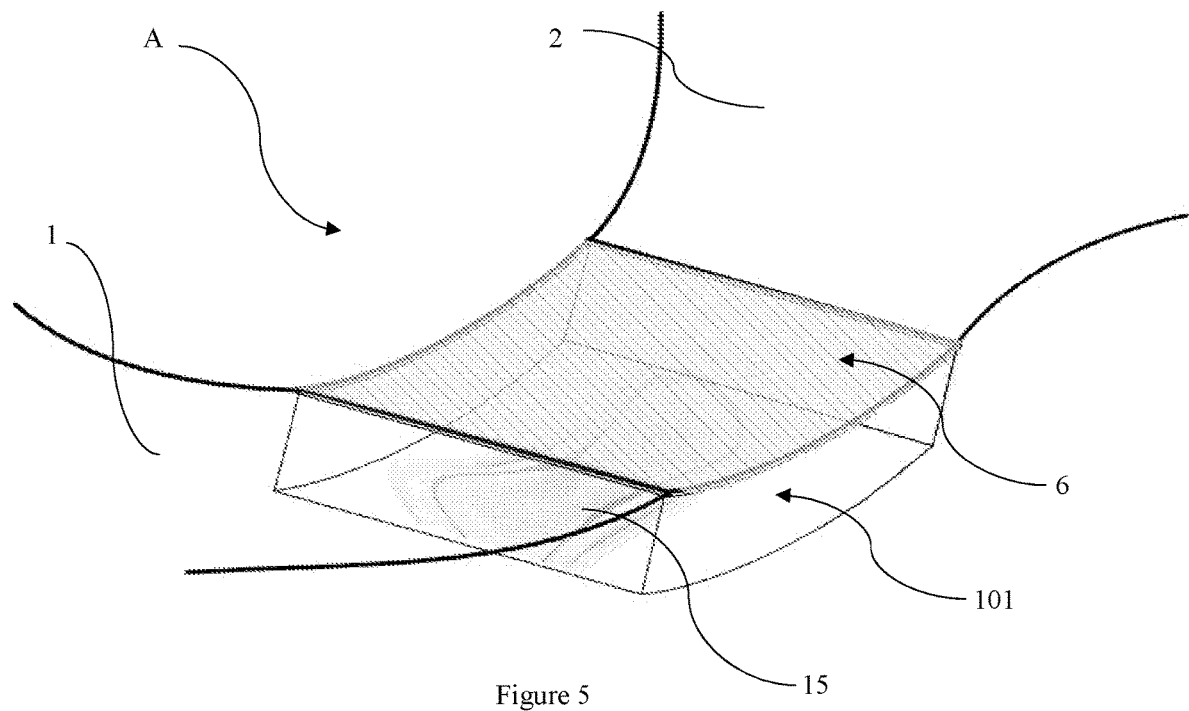
FIG. 5 shows an assembled view of the detachable pouch attached to the permeable undergarment in accordance with some embodiments of the present disclosure.

FIG. 5 shows an assembled view of the detachable pouch (101) fixed to the undergarment (100) forming the undergarment system (A). In operation, the user can at any time detach or attach the detachable pouch (101) based on requirement. Additionally, the user has the choice to dispose or reuse the undergarment (100) as disclosed in the previous paragraphs. In an embodiment, and in scenarios where the user opines that the detachable pouch (101) may not be required, the user can use the undergarment (100) as any other normal undergarment (100). During the time of attaching and detaching the detachable pouch (101), the user may have to lower the undergarment (100) up to knee lengths to configure the detachable pouch (101). In some scenarios, the user can configure the detachable pouch (101) without having to lower the undergarment (100).

Advantages of the embodiment of the present disclosure are illustrated herein.

In some embodiments, the present disclosure provides for a permeable undergarment (100) that can be used to configure a detachable pouch (101) in order to collect body fluids discharged from the user. The permeable layer (6) comprising the wicking fibres (9) wicks the body fluids and transfers the body fluids into the detachable pouch (101) for collection and absorption.

In some embodiments, the detachable pouch (101) can be simply detached and a fresh detachable pouch (101) can be readily attached to the undergarment (100).

In some embodiments, the permeable layer (6) with the wicking fibres (9) can be detached after usage, and a fresh permeable layer (6) can be readily attached to the undergarment (100).

In some embodiments, the user may opt to use the undergarment (100) as a normal everyday undergarment (100) without attaching the detachable pouch (101) thereby, providing flexibility in using protective or absorptive undergarments (100).

In some embodiments, the detachable pouch (101) that is attached on to the undergarment (100) prevents leakage of the body fluids collected therein nor does the detachable pouch (101) add any bulk to the crotch region (CR) of the undergarment (100).

In some embodiments, the user may opt to not use the at least one absorption pad (15) if the base layer (13) of the detachable pouch is configured as the absorption pad.

In some embodiments, the permeable undergarment (100) provides a combination of high functionality of disposable materials with higher normality of fabric for distinguished usage between normal undergarment and the permeable undergarment.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

REFERRAL NUMERALS

| Particulars | Referral Number |
| --- | --- |
| Permeable Undergarment | 100 |
| Detachable pouch | 101 |
| Undergarment system | A |
| First section | 1 |
| Second section | 2 |
| Waistband | 3 |
| A first leg opening | 4 |
| A second leg opening | 5 |
| A permeable layer | 6 |
| First joining edge | 7 |
| Second joining edge | 8 |
| Mesh of wicking fibres | 9 |
| A first side edge | 10 |
| A second side edge | 11 |
| Gripping layers | 12 |
| Base layer | 13 |
| Plurality of side walls | 14 |
| At least one absorption pad | 15 |
| Plurality of fasteners | 16 |
| Opening | 17 |
| Top flap | 18 |
| Bottom flap | 19 |
| Top portion | TP |
| Bottom portion | BP |
| Front side | FS |
| Rear side | RS |
| Crotch region | CR |
| Side portion | SP |
| Housing region | HR |

We claim:
1. A reusable permeable undergarment comprising:
a first section forming a front side of the undergarment, extending from a top portion to a bottom portion;
a second section provided opposite to the first section and forming a rear side of the undergarment, extending from the top portion to the bottom portion, wherein the first section and the second section are joined to a waistband at the top portion of the undergarment;
a first leg opening and a second leg opening defined in-between the first section and the second section, and on adjacent sides of a crotch region; and
a permeable layer provided at the crotch region, wherein the permeable layer connects the first section and the second section of the undergarment at the bottom portion, and allows flow of body fluids from a user through the permeable layer and out of the undergarment, and the permeable layer has a first joining edge which is directly joined along its length to the bottom portion of the first section and a second joining edge which is directly joined along its length to the bottom portion of the second section,
wherein the undergarment has provisions on an outer surface at the crotch region, at the region where the permeable layer is attached, for attaching a detachable pouch so that the body fluids discharged from the user flow through the permeable layer, out of said undergarment, and can be collected when an attached pouch is positioned in the crotch region.

2. The undergarment as claimed in claim 1, wherein the permeable layer comprises a mesh of wicking fibers to wick the body fluids off the user and transfers the body fluids through the permeable layer.

3. The undergarment as claimed in claim 1, wherein the first joining edge, the second joining edge, a first side edge and a second side edge of the permeable layer are equipped with gripping layers, to grip the permeable layer on skin of the user.

4. The undergarment as claimed in claim 1, wherein the permeable layer is detachable from the first section and the second section of the undergarment.

5. The undergarment as claimed in claim 1, wherein the first joining edge is permanently joined along its length to the bottom portion of the first section, and the second joining edge is permanently joined along its length to the bottom portion of the second section.

6. The undergarment as claimed in claim 5, wherein the first joining edge is permanently joined along its length to the bottom portion of the first section, and the second joining edge is permanently joined along its length to the bottom portion of the second section by adhesive bonding, stitching, and / or knitting.

7. The undergarment as claimed in claim 1, wherein the first joining edge is detachably joined along its length to the bottom portion of the first section, and the second joining edge is detachably joined along its length to the bottom portion of the second section.

8. The undergarment as claimed in claim 7, wherein the first joining edge is detachably joined along its length to the bottom portion of the first section, and the second joining edge is detachably joined along its length to the bottom portion of the second section by Velcro strips, detachable adhesive tapes, silicone sticky tapes, and / or snap-fitting buttons.

\* \* \* \* \*